US005739440A

United States Patent [19]
Diadelfo et al.

[11] Patent Number: 5,739,440
[45] Date of Patent: Apr. 14, 1998

[54] METHOD AND DEVICE FOR REMOVING HYDROCARBONS FLOATING ON WATER

[75] Inventors: Angelo Diadelfo; Diana Trasente, both of St.-Léonard, Canada

[73] Assignee: Environmental Remediation Equipment Inc., Anjou, Canada

[21] Appl. No.: 806,146

[22] Filed: Feb. 25, 1997

[51] Int. Cl.[6] .................................................. G01N 1/12
[52] U.S. Cl. ............................... 73/864.63; 210/538
[58] Field of Search ......................... 73/864.63; 210/767, 210/800, 242.1, 242.3, 513, 537, 532.1, 533, 538, 540

[56] References Cited

U.S. PATENT DOCUMENTS

| | | | |
|---|---|---|---|
| 2,333,711 | 11/1943 | Dwiggins | 73/864.63 |
| 4,305,303 | 12/1981 | Thies | 73/863.21 |
| 4,934,420 | 6/1990 | Radna | 210/533 |
| 5,537,881 | 7/1996 | White | 73/864.63 |
| 5,597,966 | 1/1997 | Timmons | 73/864.63 |

FOREIGN PATENT DOCUMENTS

| | | | |
|---|---|---|---|
| 667 520 | 10/1929 | France | 210/538 |

OTHER PUBLICATIONS

TIMCO Mfg., Inc., Advertising Leaflet on Groundwater Monitoring Products.

*Primary Examiner*—Robert Raevis
*Attorney, Agent, or Firm*—Swabey Ogilvy Renault

[57] ABSTRACT

The invention is concerned with a simple and inexpensive device for rapidly removing a first liquid medium floating on a second liquid medium, the first medium having a density less than the second medium and being immiscible therewith. The device of the invention comprises an immersible container means having a bottom opening, a valve for allowing the first and second media to flow into the container through the bottom opening upon immersing the container into the first and second media and for controllably preventing the first medium from draining from the container upon raising the container out of the media, a float member having a density greater than the density of the first medium and less than the density of the second medium, the float member being mobile in the container to move up and down with an interface between the first and second media. The valve is controlled by the float member to cause closing of the valve when the second medium has substantially completely drained from the container, thereby retaining the first medium in the container.

15 Claims, 1 Drawing Sheet

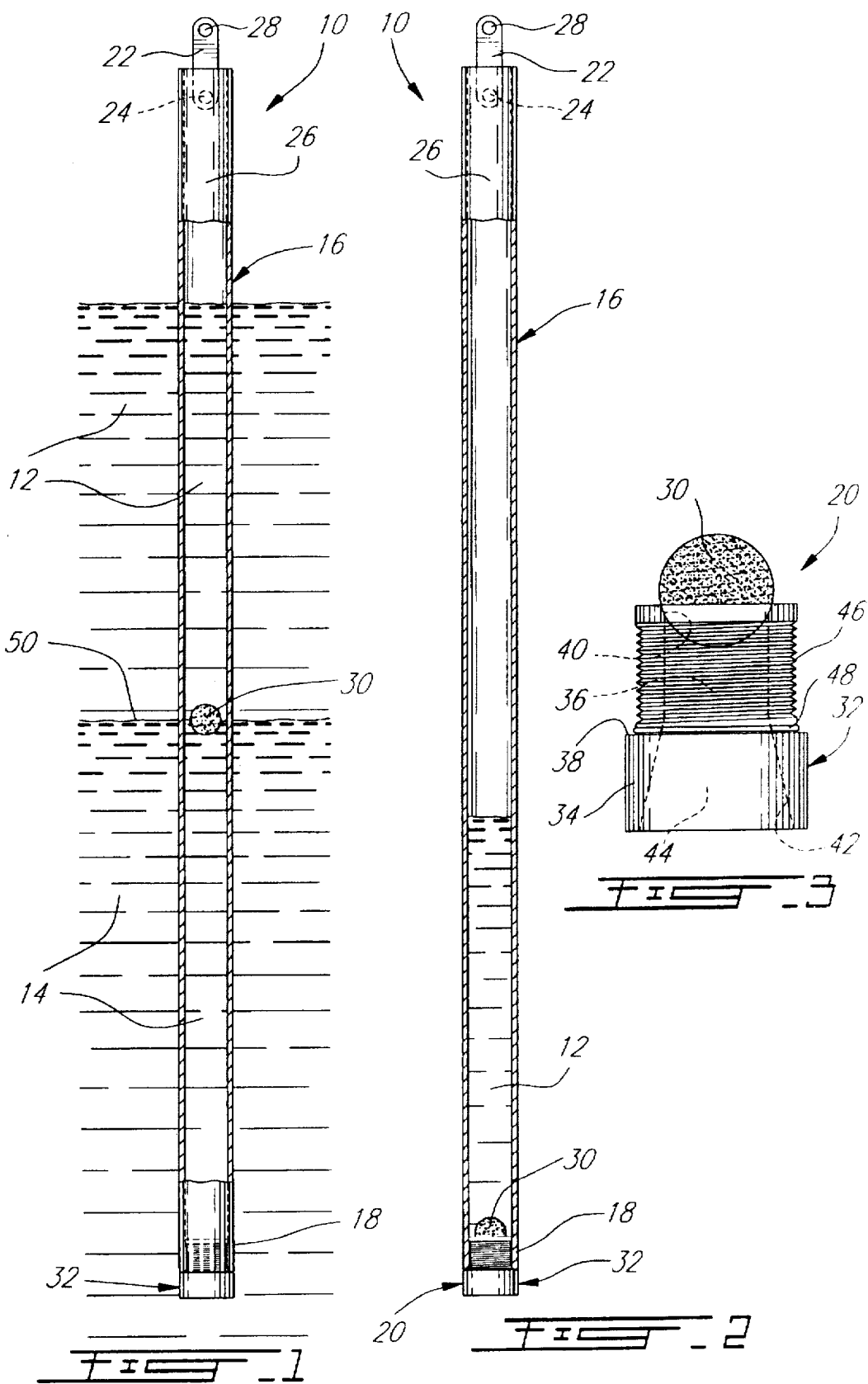

METHOD AND DEVICE FOR REMOVING HYDROCARBONS FLOATING ON WATER

BACKGROUND OF THE INVENTION

The present invention relates to a method and device for removing a first liquid medium floating on a second liquid medium. More particularly, the invention is directed towards the removal or sampling of light, non-aqueous phase liquids present in groundwater or waste water.

Light, non-aqueous phase liquids are hydrocarbon contaminants which float on water. The most common of these are toluene, benzene, ethyl benzene, diesel, kerosene, gasoline, crude oil and petroleum oil. Various devices have been proposed for removing such hydrocarbons from groundwater or waste water. For instance, use can be made of a passive skimmer which is designed to float on the oil/water interface in the groundwater. The passive skimmer consists of a slitted tube with an oleophilic membrane in its interior. This special membrane allows only the oil or hydrocarbon to enter without the water. The oil or hydrocarbon that enters the skimmer collects at the bottom of the tube. Depending on the type of hydrocarbon to be removed, the skimmer can take a few hours to fill up. Other systems require either electricity or compressed air to remove hydrocarbons from the groundwater, and are very costly.

SUMMARY OF THE INVENTION

It is therefore an object of the present invention to overcome the above drawbacks and to provide a method and device which can rapidly remove light, non-aqueous phase liquids from groundwater or waste water, in a simple and inexpensive manner.

In accordance with the present invention, there is thus provided a device for removing a first liquid medium floating on a second liquid medium, the first medium having a density less than the second medium and being immiscible therewith. The device of the invention comprises an immersible container means having a bottom opening, a valve means for allowing the first and second media to flow into the container means through the bottom opening upon immersing the container means into the first and second media and for controllably preventing the first medium from draining from the container means upon raising the container means out of the media, and a float means having a density greater than the density of the first medium and less than the density of second medium, the float means being mobile in the container means to move up and down with an interface between the first and second media. The valve means is controlled by the float means to cause closing of the valve means when the second medium has substantially completely drained from the container means, thereby retaining the first medium in the container means.

According to a preferred embodiment of the invention, the immersible container means is an immersible tube means and the valve means is a check-valve means disposed at a lower end of the tube means. The check-valve means comprises seat means and stopper means displaceable relative to the seat means between a closed position of the check-valve means whereat the stopper means is seated on the seat means and an open position of the check-valve means whereat the stopper means is separated from the seat means, the aforesaid float means defining the stopper means. When the tube means is immersed in the first and second media, the stopper means is displaced to the open position by the first and second media to allow entry of the media into the tube means and formation of the aforesaid interface between the first and second media. When the tube means is raised out of the media, the second medium drains out of the tube means, the stopper means floating on the interface at least when the interface approaches the seat means so that the stopper means is displaced to the closed position when the interface reaches the seat means, thereby retaining the first medium in the tube means.

Where the first medium comprises at least one hydrocarbon having a specific gravity less than about 1 at 20° C. and the second medium is water, the stopper means is preferably a ball made of a plastic material which is resistant to attack by the hydrocarbon and has a specific gravity of about 0.9 at 20° C. Examples of suitable plastic materials which can be used include polypropylene (specific gravity=0.91), ultra high molecular weight polyolefin (specific gravity=0.94), high density polyethylene (specific gravity=0.96), medium density polyethylene (specific gravity=0.94), low density polyethylene (specific gravity=0.92), very low density polyethylene (specific gravity=0.90), high hardness polyethylene (specific gravity=0.94) and low hardness polyolefin (specific gravity=0.93). Polypropylene is particularly preferred.

According to another preferred embodiment, the check-valve means include a check member having a cylindrical body with an axial bore defining a passage for the first and second media- The body has a frusto-conical inner wall extending along an upper portion of the bore and defining the seat means for receiving the ball in sealing contact engagement when the ball is displaced to the closed position- preferably, the body also has a frusto-conical inner wall extending along a lower portion of the bore and defining a downwardly flaring passage for enhancing flow of the second medium during drainage from the container means.

The present invention further provides, in another aspect thereof, a method of removing a first liquid medium floating on a second liquid medium, the first medium having a density less than the second medium and being immiscible therewith. The method of the invention comprises the steps of:

a) immersing an immersible container means having a bottom opening into the first and the second media to allow the first and the second media to flow into the container means: through the bottom opening;

b) raising the container means out of the first and second media to cause the second medium to drain from the container means;

c) closing the bottom opening to prevent the first medium from passing therethrough when the second medium has substantially completely drained; and d) removing the first medium from the container means.

Preferably, the method according to the invention further includes the steps of:

e) providing a valve means in the bottom opening;

f) providing a float means having a density greater than the density of the first medium and less than the second medium, the float means being mobile in the container means to move up and down with an interface between the first and second media; and g) using the float means to close the valve means when the second medium has substantially completely drained from the container means.

BRIEF DESCRIPTION OF THE DRAWINGS

Further features and advantages of the invention will become more readily apparent from the following description of a preferred embodiment illustrated by way of example in the accompanying drawings, in which:

FIG. 1 is a part-sectional elevation view of a device according to a preferred embodiment of the invention, shown immersed in groundwater contaminated with light, non-aqueous phase liquids (hereinafter referred to as "LNAPs") floating on the water;

FIG. 2 is a part-sectional elevation view of the device illustrated in FIG. 1, shown raised out of the contaminated groundwater and with the LNAPs trapped therein; and FIG. 3 is an elevation view of the ball check-valve used in the device illustrated in FIGS. 1 and 2.

DESCRIPTION OF PREFERRED EMBODIMENTS

Referring to FIGS. 1 and 2, there is illustrated a device 10 for removing LNAPs 12 from groundwater 14. The device 10 comprises an elongated tube 16 provided at its lower end 18 with a ball check-valve 20, the tube 16 being made of a plastic material which is resistant to attack by hydrocarbons. An attachment member 22 is connected to a rod 24 which extends transversely of the tube 16 at its upper end 26. The member 22 is provided with an aperture 28 enabling one to attach a rope for lowering the device 10 to a desired depth in a well.

As shown in FIG. 3, the ball check-valve 20 comprises a ball 30 and a check-member 32 having a generally cylindrical body 34 with an axial bore 36 and a shoulder 38. The body 34 has a frusto-conical inner wall 40 extending along an upper portion of the bore 36 and defining a seat for receiving the ball 30 in sealing contact engagement. The body 34 also has a frusto-conical inner wall 42 extending along a lower portion of the bore 36 and defining downwardly flaring passage 44. The check-member 32 is removably fixed to the lower end 18 of the tube 16 by means of threads 46 engaging corresponding threads (not shown) formed in the inner wall of the tube 16. An O-ring 48 sitting on the shoulder 38 is provided to prevent liquid from leaking between the lower extremity of the tube 16 and the shoulder 38.

The ball 30 has a density greater than the density of the LNAPs 12 and less than the density of the water 14 so as to float on the interface 50 between the two liquid media. It is made of a material which is resistant to attack by hydrocarbons. The ball 30 is preferably made of polypropylene which has a specific gravity of 0.91 at 20° C. It is also possible to use a hollow ball made of a material having a specific gravity greater than 1, such as polyvinylchloride, since the overall density of such a ball would be less than the density of water.

When it desired to remove or sample the LNAPs 12 floating on the groundwater 14, the device 10 is immersed into the two liquid media 12,14, as shown in FIG. 1. Due to the particular density of the ball 30, the liquid media 12,14 upon passing through the bore 36 in the check member 32 cause the ball 30 to separate from the seat 40, thereby opening the valve 20. The liquid media 12,14 thus flow into the tube 16 with minimal turbulence so that the interface 50 between the two media 12 and 14 is reformed inside the tube 16, with the ball 30 floating on the interface 50. The device 10 is then raised out of the media 12,14, causing the water 14 to drain out of the tube 16 through the bore 36 of check-member 32 and also causing the interface 50 with the ball 30 to move downwardly. The provision of a downwardly flaring passage 44 enhances the flow of the water during the drainage. When the interface 50 reaches the seat 40, the ball 30 sits on the seat and closes the valve 20, thereby preventing the LNAPs 12 from passing through the bore 36. As a result, essentially water-free LNAPs 12 are obtained in the tube 16, as shown in FIG. 2. The water-free LNAPs thus obtained can be removed from the tube 16 by tilting the tube so as to discharge the same through the other end 26 of the tube 16.

We claim:

1. A device for removing a first liquid medium floating on a second liquid medium, said first medium having a density less than said second medium and being immiscible therewith, said device comprising:

an immersible container means having a bottom opening;

a valve means for allowing said first and second media to flow into said container means through said bottom opening upon immersing said container means into said first and second media and for controllably preventing said first medium from draining from said container means upon raising said container means out of said media; and a float means having a density greater than the density of said first medium and less than the density of said second medium, said float means being mobile in said container means to move up and down with an interface between said first and second media;

said valve means being controlled by said float means to cause closing of said valve means when said second medium has substantially completely drained from said container means, thereby retaining said first medium in said container means.

2. A device as claimed in claim 1, wherein said immersible container means is an immersible tube means and said valve means is a check-valve means disposed at a lower end of said tube means, said check-valve means comprising seat means and stopper means displaceable relative to said seat means between a closed position of said check-valve means whereat said stopper means is seated on said seat means and an open position of said check-valve means whereat said stopper means is separated from said seat means, and wherein said float means defines said stopper means, whereby when said tube means is immersed in said first and second media, said stopper means is displaced to said open position by said first and second media to allow entry of said media into said tube means and formation of said interface between said first and second media, and when said tube means is raised out of said media, said second medium drains out of said tube means, said stopper means floating on said interface at least when said interface approaches said seat means so that said stopper means is displaced to said closed position when said interface reaches said seat means, thereby retaining said first medium in said tube means.

3. A device as claimed in claim 2, wherein said first medium comprises at least one hydrocarbon having a specific gravity less than about 1 at 20° C. and said second medium is water, and wherein said stopper means is a ball made of a plastic material which is resistant to attack by said at least one hydrocarbon and has a specific gravity of about 0.9 at 20° C.

4. A device as claimed in claim 3, wherein said plastic material is selected from the group consisting of polypropylene, ultra high molecular weight polyethylene, high density polyethylene, medium density polyethylene, low density polyethylene, very low density polyethylene and polyolefin.

5. A device as claimed in claim 4, wherein said plastic material is polypropylene.

6. A device as claimed in claim 3, wherein said check-valve means includes a check member having a cylindrical body with an axial bore defining a passage for said first and second media.

7. A device as claimed in claim 6, wherein said body has a frusto-conical inner wall extending along an upper portion of said bore and defining said seat means for receiving said ball in sealing contact engagement when said ball is displaced to said closed position.

8. A device as claimed in claim 6, wherein said body also has a frusto-conical inner wall extending along a lower portion of said bore and defining a downwardly flaring passage for enhancing flow of said second medium during drainage from said container means.

9. A device as claimed in claim 2, wherein said check-valve means is removably fixed to the lower end of said tube means.

10. A method of removing a first liquid medium floating on a second liquid medium, said first medium having a density less than said second medium and being immiscible therewith, said method comprising the steps of:

a) immersing an immersible container means having a bottom opening into said first and said second media to allow said first and said second media to flow into said container means through said bottom opening;

b) raising said container means out of said first and second media to cause said second medium to drain from said container means;

c) closing said bottom opening to prevent said first medium from passing therethrough when said second medium has substantially completely drained; and d) removing said first medium from said container means.

11. A method as claimed in claim 10, further including the steps of:

e) providing a valve means in said bottom opening;

f) providing a float means having a density greater than the density of said first medium and less than said second medium, said float means being mobile in said container means to move up and down with an interface between said first and second media; and g) using said float means to close said valve means when said second medium has substantially completely drained from said container means.

12. A method as claimed in claim 11, wherein said immersible container means is an immersible tube means and said valve means is a check-valve means disposed at a lower end of said tube means, said check-valve means comprising seat means and stopper means displaceable relative to said seat means between a closed position of said check-valve means whereat said stopper means is seated on said seat means and an open position of said check-valve means whereat said stopper means is separated from said seat means, and said float means defining said stopper means, and wherein in step (a) said stopper means is displaced to said open position by said media to allow entry of said media into said tube means and formation of said interface between said first and second media, and in step (b) said stopper means floating on said interface at least when said interface approaches said seat means so that said stopper means is displaced to said closed position when said interface reaches said seat means, thereby retaining said first medium in said tube means.

13. A method as claimed in claim 12, wherein said first medium comprises at least one hydrocarbon having a specific gravity less than about 1 at 20° C. and said second medium is water, and wherein said stopper means is a ball made of a plastic material which is resistant to attack by said at least one hydrocarbon and has a specific gravity of about 0.9 at 20° C.

14. A method as claimed in claim 13, wherein said plastic material is selected from the group consisting of polypropylene, ultra high molecular weight polyethylene, high density polyethylene, medium density polyethylene, low density polyethylene, very low density polyethylene and polyolefin.

15. A method as claimed in claim 14, wherein said plastic material is polypropylene.

* * * * *